United States Patent [19]

Risgin et al.

[11] B 4,008,394

[45] Feb. 15, 1977

[54] GAS ANALYZING

[75] Inventors: Ojars Risgin, Grass Lake; Charles B. Arnold, Saline, both of Mich.

[73] Assignee: Sensors, Inc., Ann Arbor, Mich.

[22] Filed: June 28, 1973

[21] Appl. No.: 374,553

[44] Published under the second Trial Voluntary Protest Program on March 30, 1976 as document No. B 374,553.

[52] U.S. Cl. .............................. 250/345; 250/344; 250/343
[51] Int. Cl.² .................................... G01N 21/00
[58] Field of Search ............... 250/343, 344, 345; 356/246

[56] References Cited
UNITED STATES PATENTS

| | | | |
|---|---|---|---|
| 2,904,687 | 9/1959 | Sobcov et al. | 250/343 |
| 2,938,118 | 5/1960 | Martin | 250/345 |
| 3,162,761 | 12/1964 | Luft | 250/344 |
| 3,498,132 | 3/1970 | Smith et al. | 250/343 |
| 3,562,524 | 2/1971 | Moore | 250/343 |
| 3,569,696 | 3/1971 | Karlson | 250/344 |
| 3,659,941 | 5/1972 | Tong | 250/344 |
| 3,678,262 | 7/1972 | Herrmann | 250/343 |
| 3,678,269 | 7/1972 | Malek | 250/343 |

Primary Examiner—Archie R. Borchelt
Assistant Examiner—B. C. Anderson
Attorney, Agent, or Firm—Shanley, O'Neil and Baker

[57] ABSTRACT

Dual-beam comparison of gas absorption characteristics in which a single source and single detector of radiant energy and single chopper disc are used in sample gas and reference gas paths. Ambient atmosphere or gas directed through a sample gas chamber can be analyzed. Multiple gas analyses, of a plurality of gases or a plurality of constituents of a gas, can be performed simultaneously utilizing the single chopper disc with a plurality of optical gas assemblies. Each such assembly includes a single source of radiant energy, means for directing the radiant energy along sample and reference gas paths to a single detector for such radiant energy. The multiple units are mounted so that the single chopper disc cyclically interrupts radiant energy in the respective sample and reference gas paths in predetermined phase relationship. The combined sample gas and reference gas path response of the single detector for each gas analyzing unit is directed to phase-sensitive signal-separation circuit means. The single chopper disc is also used to generate phase reference signals for gating the phase-sensitive signal separation circuit means to produce a voltage output for the sample and reference gas paths, $V_s$ and $V_r$, respectively. An automatic gain control function, to eliminate or minimize variations in source intensity, detector characteristics, and circuit components influencing both gas paths equally, is provided by electronic ratio circuit means or feedback circuit means.

18 Claims, 23 Drawing Figures

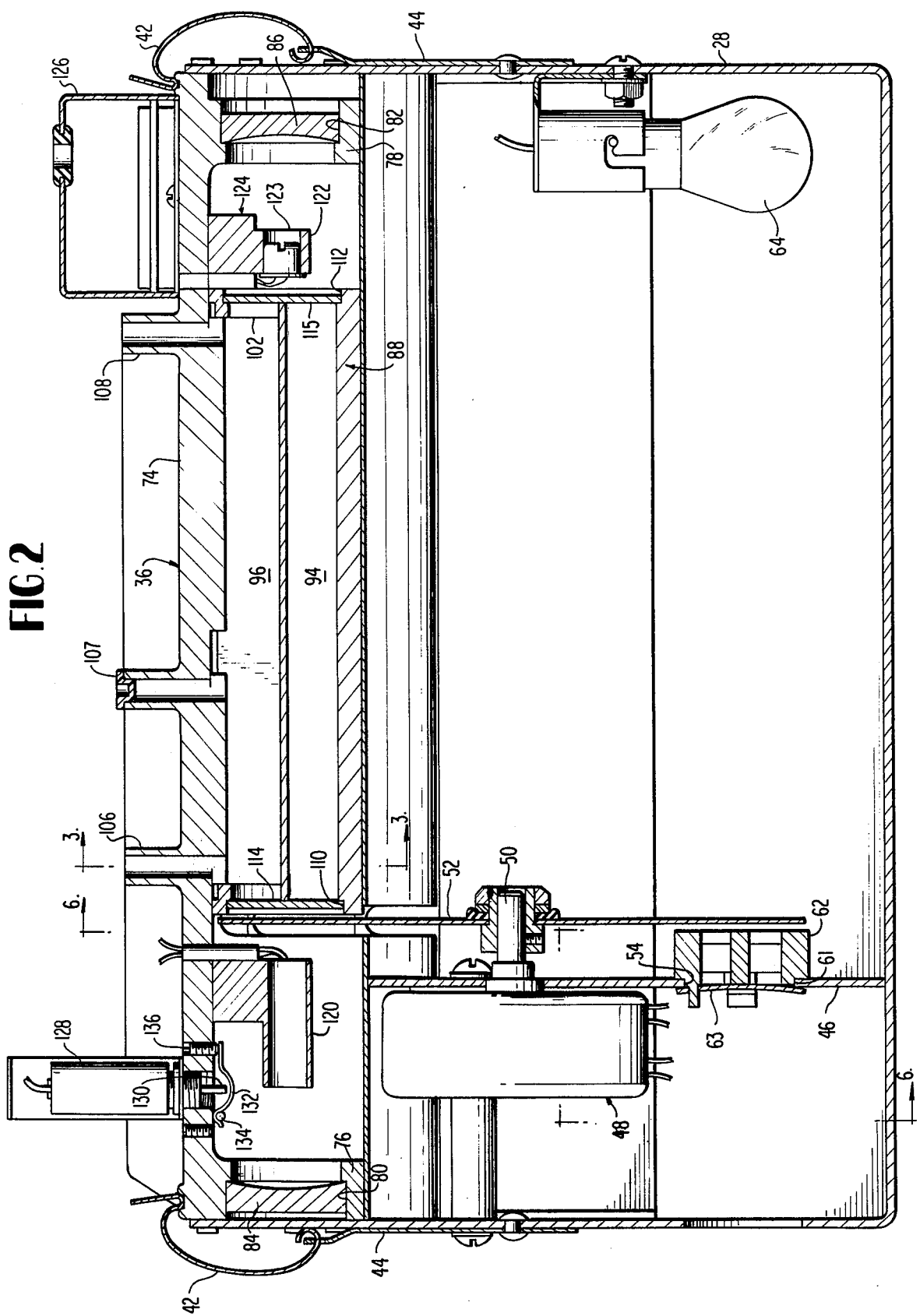

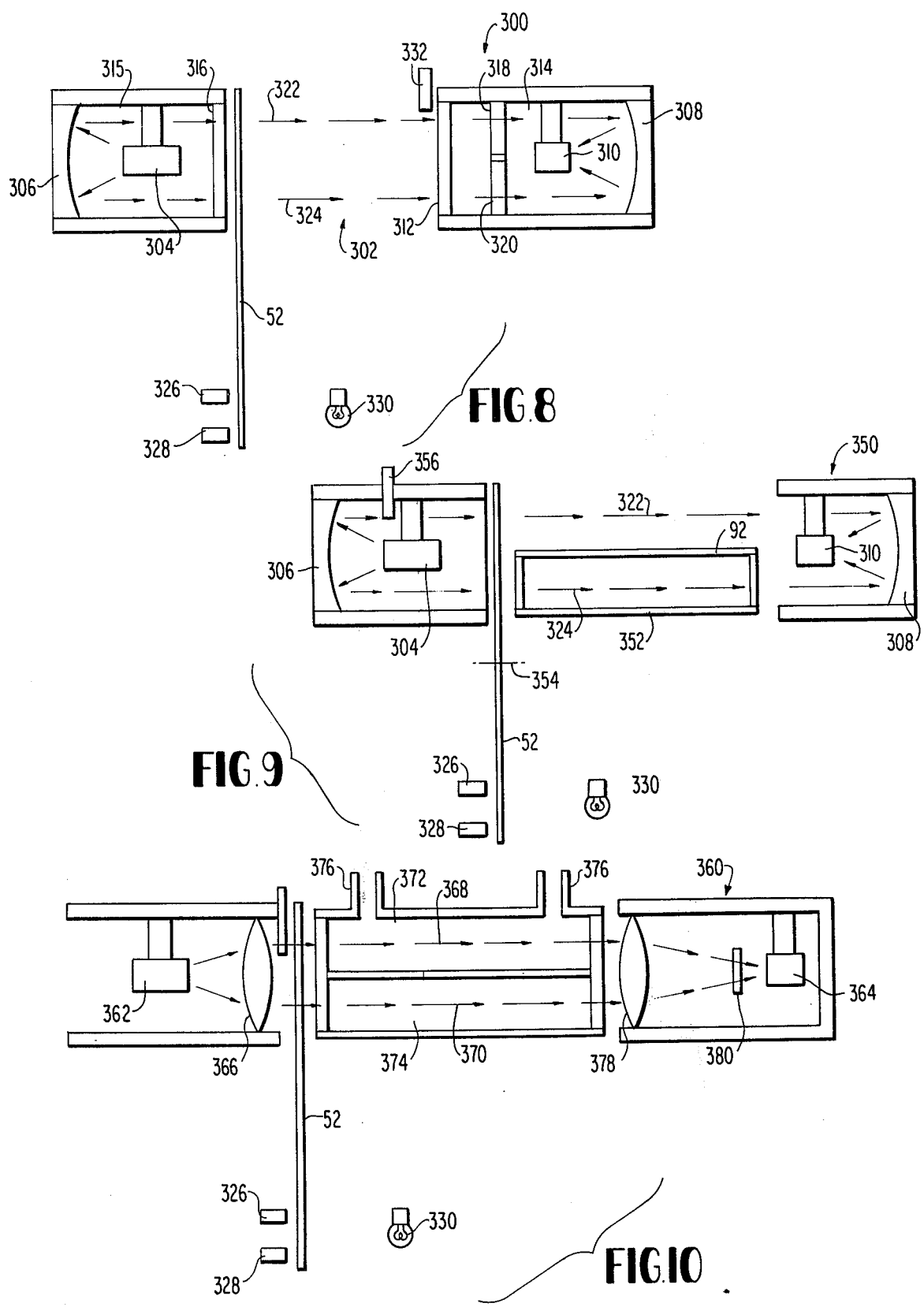

GAS ANALYZING

The invention relates to gas analyzing. More particularly the invention relates to gas analyzing structure utilizing a single source of radiant energy and a single detector for comparison-type dual-beam analysis of a test gas.

The invention includes multiple unit gas analyzer structure using a single rotary chopper common to a plurality of absorption-type gas analysis assemblies each including a single source of radiant energy and a single detector for such radiant energy. Specific aspects of cell structure for defining sample and reference gas chambers and associated apparatus are described and claimed in a copending application entitled "Apparatus for Gas Analysis", filed by Ojars Risgin, Charles B. Arnold, Peter A. Hubbard, and Edward D. Scarborough filed concurrently with the present application and assigned to a common assignee.

Many prior art commercial gas analyzers employ a Luft cell, the capacitance of which is changed by infrared induced pressure charges. Such prior art analyzers require careful mounting for vibration and thermal insulation and are not as suitable for rugged-use applications as the present invention. Also many prior art types of dual-beam instruments commonly use dual detectors which inherently present problems of matching and thermal balancing. Such problems are eliminated by the single source and single detector teachings of the present invention and the mechanical arrangement and electronic features of the present invention.

This invention provides a fast response time, accurate, radiation-absorption comparison-type gas analyzer which disposes a reference gas and sample gas path in contiguous aligned relation. Radiant energy from a single source of radiant energy passes along both paths simultaneously to a single detector for such radiant energy. A unique chopper arrangement is an important part of the multi-unit concept of the present invention and contributes to the phase sensitive separation of electrical signals representative of the sample and reference gases. It makes practical the use of separate frequencies and/or separate phase relationship in each gas path to implement electronic separation. A novel automatic gain control function utilizes electronic ratio means or feedback circuitry to compensate for variations in source intensity, attenuation in the optical path, and component variations which affect both the sample and reference gas paths.

The multi-unit gas analyzer concept of the present invention which disposes a plurality of gas analyzer units in predetermined positions to be operative with a single chopper disc permits analysis of a plurality of gases or analysis of a plurality of gas constituents simultaneously.

Other features and advantages of the invention will be considered during a detailed description of the invention using infrared as the radiant energy attenuated by the gas of interest. The accompanying drawings, briefly identified below, form part of such detailed description.

FIG. 1 is a perspective view, with portions cut away, of a specific multi-unit gas analyzer apparatus presented for explaining the basic multiple gas analyses concept of the present invention, FIG. 2 is a detailed cross-sectional view along the mid-section of the apparatus of FIG. 1, FIG. 3 is a cross-sectional view of gas cell structure taken along the lines 3—3 of a portion of FIG. 2, FIG. 4 is a plan view of a chopper disc for dual-frequency dual-phase operation in accordance with the invention, FIG. 5 is a plan view of a chopper disc for single-frequency dual-phase operation in accordance with the invention, FIG. 6 is a sectional view in elevation, with portions cut away for clarity, taken along the lines 6—6 of FIG. 2, FIG. 7 is a schematic diagram of circuitry providing phase sensitive separation of sample and reference path signals in accordance with the invention.

FIGS. 7A through 7J are graphical representations of values during one cycle rotation of a chopper disc utilizing the separation circuitry of FIG. 7, in which:

FIG. 7A depicts sample gas path window exposure,

FIG. 7B depicts reference gas path window exposure,

FIG. 7C depicts detector voltage response to IR in the sample gas path only,

FIG. 7D depicts detector voltage response to IR in the reference gas path only,

FIG. 7E depicts the total detector output voltages,

FIG. 7F depicts window exposure of a phototransistor for the sample gas path,

FIG. 7G depicts window exposure of a phototransistor for the reference gas path, FIG. 7H depicts the voltage of the sample gas path electrical channel means resulting in a net output of $V_s$, FIG. 7J depicts the voltages of the reference gas path electrical channel means resulting in a net output of $V_r$.

Figure 14:
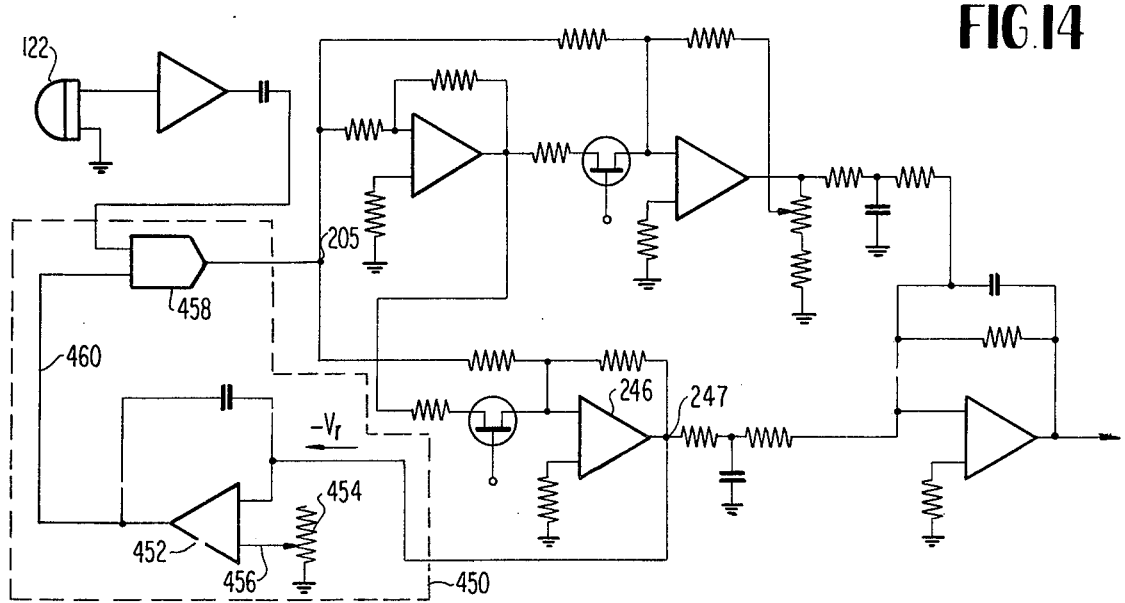
Figure 7:
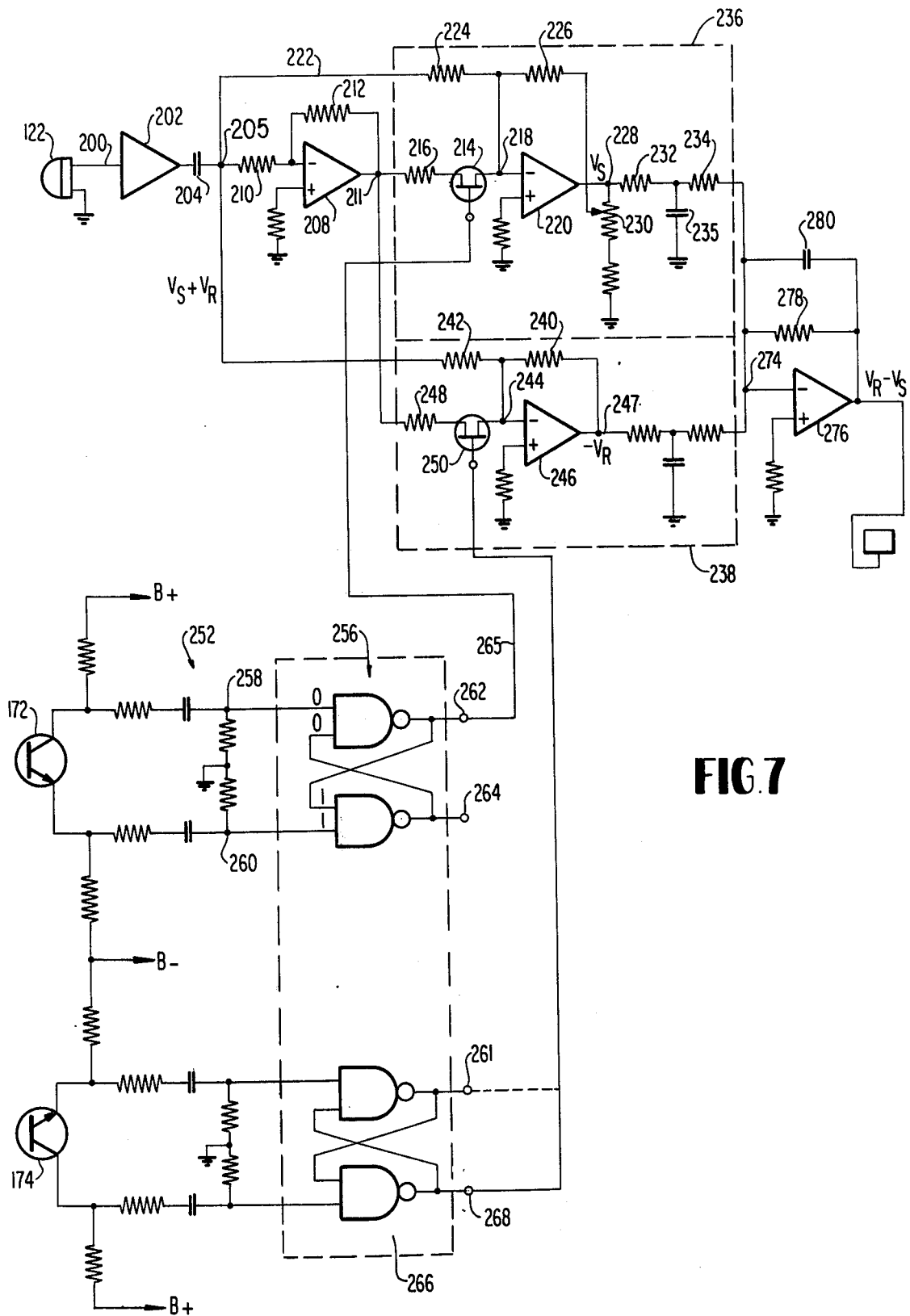
Figure 11:
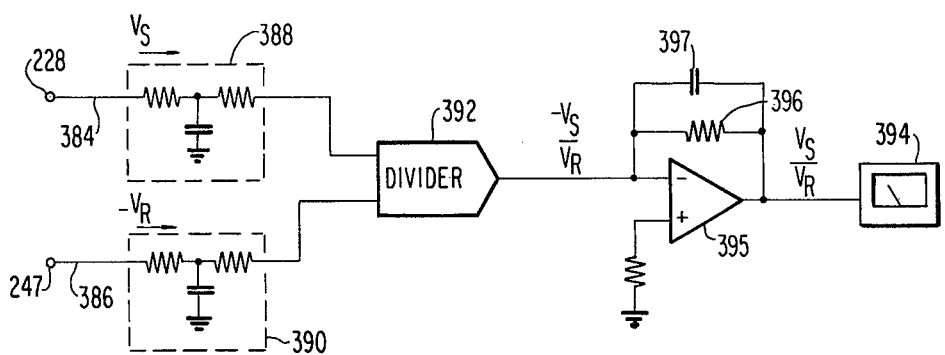
Figure 12:
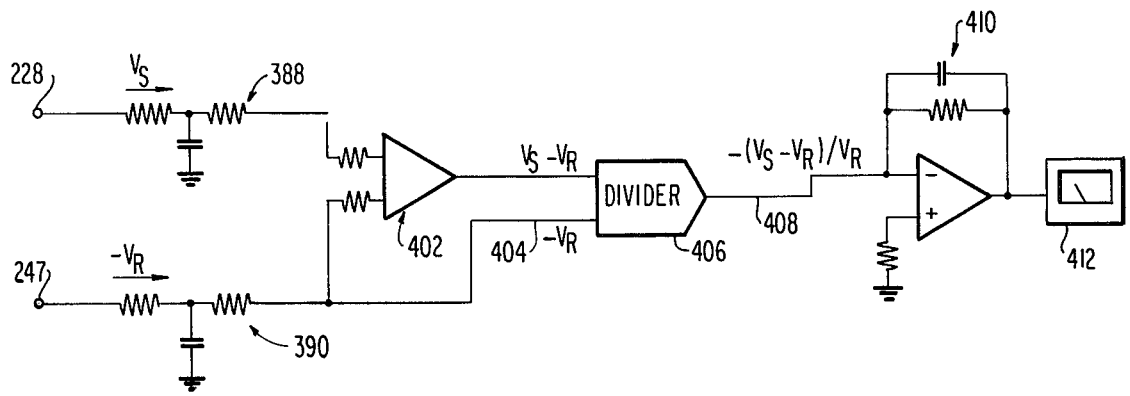
Figure 13:
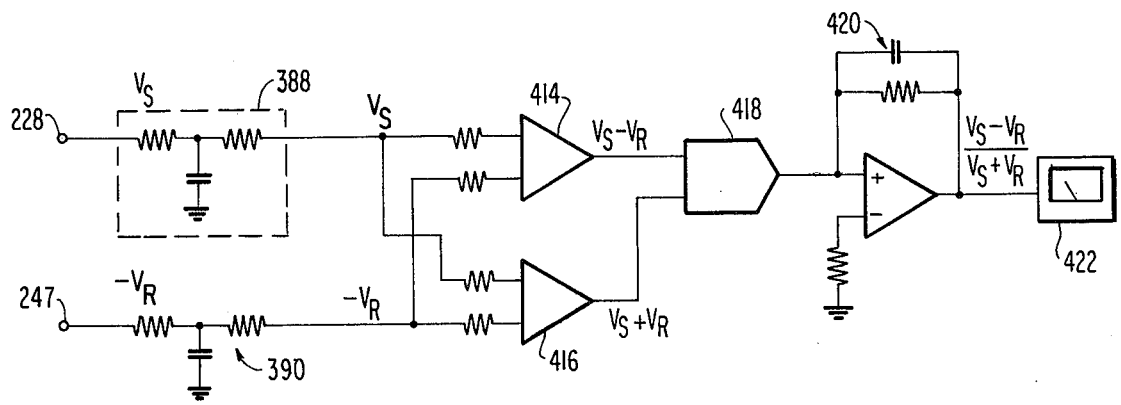

FIG. 8 is a schematic presentation of a novel arrangement for ambient gas analysis, FIG. 9 is a schematic presentation of a novel arrangement for ambient gas analysis utilizing a reference gas chamber, FIG. 10 is a schematic presentation of a novel arrangement utilizing sample and reference gas cells and collimating lenses, FIGS. 11, 12, and 13 are schematic diagrams of separate circuits embodying the invention for use with the circuit of FIG. 7 for determining selected mathematical functions, and FIG. 14 is a schematic diagram of feedback circuitry embodying the invention.

Figure 1:
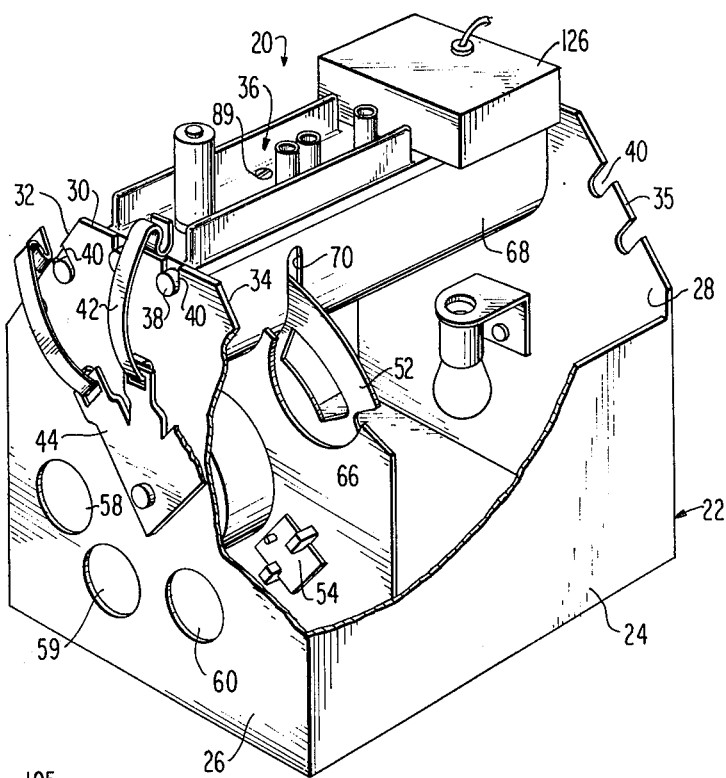

Referring to FIGS. 1 and 2, gas analyzer device 20 has a frame-like housing 22 with side walls 24, a front wall 26, and a rear wall 28. The upper portion of front wall 26 presents a centrally-located horizontal edge 30. Sloping edges 32 and 34 depend downwardly and outwardly in angled relation to horizontal edge 30. The upper portion of rear wall 28 is similarly formed.

Gas analyzer unit 36 is supported by front and rear walls 26 and 28. Support pins 38 extending from gas analyzer unit 36 seat in upwardly opening slots 40 formed in top edge 30 of front wall 26. Similar pins (not shown) cooperate with like slots at the top edge of rear wall 28. Spring clips connected to a mounting plate 44 on the respective front and rear walls 26 and 28 provide for releasably securing analyzer units, such as 36, to housing 22.

In spaced relation from front wall 26 is a motor support partition 46 which is secured between side walls 24. Mounted on partition 46 is a chopper disc drive motor 48 having a shaft 50 which extends through the partition. Circular chopper disc 52 is secured to shaft 50. An arcuate slot 54 lying along a circumferential path about the axis of rotation of chopper disc 52 is formed in partition 46. Slot 54 extends a substantial distance across the partition in general alignment with access openings 58-60 in front wall 26. Slot 54 provides for adjustably mounting one or more phototransistor support blocks 62 in a predetermined circumferential position relative to chopper disc 52. Phototransistor support blocks 62 are secured to the partition with retaining clips 63. Mounted on rear wall 28 is a lamp bulb 64 which provides a common source of light for phototransistors mounted on the phototransistor block 62.

To carry out the multiple-unit concept of the present invention accommodation is made for a plurality of units in the specific apparatus shown. Note in FIG. 1 that sloping edge 35 of rear wall 28 has upwardly opening positioning slots 40 as described earlier and, that sloping edge 32 of front wall 26 has similar slots 40. It will be understood that the sloping edge parallel with front edge 32 (not shown in FIG. 1) and the sloping front edge 34 also have positioning slots 40. This arrangement enables placing two additional optical gas analysis assemblies, similar to analyzer unit 36, on housing 22 along an arcuate path in circumferential relationship to the axis of rotation of chopper disc 52 so the multiple unit analyzer device 20 can be used to simultaneously analyze several different gases, or determine several different constituents of the same gas. To accommodate several analyzer units partition 46 has its top edge scalloped as at 66 at several locations to receive the U-shaped cover 68 of each analyzer unit. Cover 68 has a transverse slot 70 formed to accommodate passage of chopper disc 52. Other units placed on the device have similar transverse slots and are operative and coact with the same single chopper disc 52.

Structural details of a gas analyzer unit are shown in FIG. 2. Analyzer unit 36 includes a rigid support plate 74 with various unitary components and removably integral cell structure. At each end of support plate 74 are unitary optical structure support brackets 76 and 78 each having a generally U-shaped periphery and counterbored openings 80 and 82, respectively. The openings 80 and 82 have their axes precisely aligned so the axes of concave mirrors 84 and 86 mounted in the respective bores have their focal axes coincident.

Figure 3:
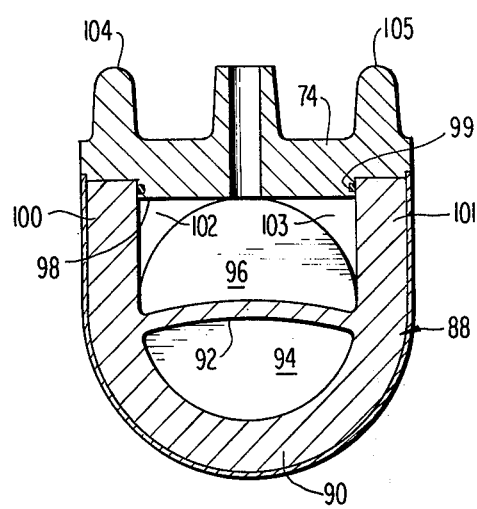

Cell structure 88 is secured, by means such as bolt 89 in FIG. 1, to support plate 74 at a location spaced from ends 76 and 78. Cell structure 88 can be unitary construction and, as shown in FIG. 3, is generally U-shaped with a rounded bottom 90. Arcuately curvilinear divider 92 divides the cell assembly into a lower chamber 94 and an upper chamber 96. Upper chamber 96 can have an open top which is closed by support plate 74. As shown this closure comprises a generally rectangular projecting block portion 98 dimensioned to provde with gasket 99 a close fit between the upper side walls 100 and 101 for gas-tight sealing.

As shown in FIG. 3, partitions 102 and 103 provide a generally half-moon configuration in cross section for chamber 96 similar to, but slightly larger than, chamber 94. Partitions 102, 103 are located at the longitudinal ends of chamber 96. Support plate 74 has upwardly extending strengthening ribs 104, 105 at each longitudinal side which add beam strength to the plate which serves as the "backbone" for the unit. As seen in FIGS. 2 and 3, gas supply ports 106-108 are formed in support plate 74 and open into upper chamber 96 of cell structure 88. These provide for introduction or flow of a sample gas to be tested, for example, through port 106 into chamber 96 and out of port 108 during operation of the apparatus.

Counterbored openings 110 and 112 at the ends of cell assembly 88 provide seats for transparent circular configuration gas chamber windows 114, 115 which close the respective ends of both lower chamber 94 and upper chamber 96. Gas chamber windows 114, 115 are cemented to longitudinal ends, including the divider means 92 to provide gas-tight sealing. Lower chamber 94 can be filled with a reference gas of known composition and this gas is sealed in the lower or reference gas chamber 94 by windows 114, 115. The sample gas to be analyzed flows through upper or sample gas chamber 96 through respective ports 106 and 108 which are located closely adjacent the opposite ends of the cell assembly.

The forward end of cell structure 88 is clearly adjacent chopper disc 52. A single source of infrared radiation 120 is secured to support plate 74 between chopper disc 52 and mirror 84. The source of infrared radiation 120 can be of the black-body, resistance wire heated type. Infrared source 120 is mounted with its axis coincident with the axes of mirrors 84 and 86.

Infrared detector 122 is located between mirror 86 and the rearward end of cell structure 88. Infrared detector 122 is secured to the underside of support plate 74 by a mounting block 124. The mounting blocks for the infrared source 120 and infrared detector 122 are each relatively narrow as viewed axially to avoid significant blocking of infrared rays from source 120 which are reflected by mirror 84 to mirror 86 and then onto detector 122. Advantageously, the heated element of infrared source 120 is mounted at the focal point of concave mirror 84 and the detector element of detector 122 is similarly mounted at the focal point of concave mirror 86.

Support plate 74 also supports housing 126 (upper right in FIG. 2) for the electronic amplifier for gas analyzer unit 36. Solenoid 128 is mounted at the opposite end of the support plate 74 above infrared source 120. Solenoid 128 includes a plunger 130 which is located adjacent to a combination calibration and test tab 132. Tab 132 is spring urged to its retracted position shown in FIG. 2 by a suitable spring located at hinge pin 134. This normally maintains the tab in engagement with adjustment screw 136, accessible through plate 174, which permits varying the position of the tab in the path of travel of infrared radiation from mirror 84 for balancing. In addition, when solenoid 128 is energized, plunger 130 moves tab 132 downwardly into the path of travel of infrared radiation from mirror 84. Only the radiation passing through sample cell 96 is affected by the position of tab 132. To balance the instrument initially, screw 136 is adjusted so that the sample and reference gas paths are balanced in the absence of any absorbing gas in the sample path. After the zerobalancing adjustment, solenoid 128 can be selectively actuated to block a predetermined portion of the sample path radiation to attenuate the sample beam an amount equivalent to a known percentage gas absorption. A calibration adjustment can then be made to bring the output meter to the proper reading, in effect adjusting the gain of the system.

Figure 4:
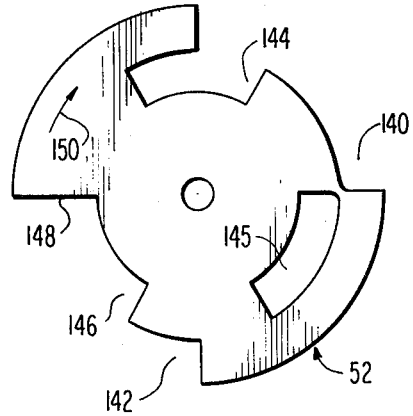

As shown in FIG. 4, chopper disc 52 includes two outer windows 140 and 142, each extending 90° circumferentially and located 180° out of phase with respect to each other. There are also three windows 144-146 each extending 60° circumferentially and located 120° out of phase with respect to each other. The configuration of the inner windows and outer windows in such that edge 148 is common to both outer slot 142 and inner slot 146. When viewed from the front as in FIG. 4, disc 52 is rotated clockwise in the direction of arrow 150. By virtue of the two outer windows 140 and 142 and the three inner windows 144-146, chopper blade 52 provides dual frequency exposure when rotated in the sample and reference paths, i.e. interrupting the infrared radiation passing through the reference chamber 94 and sample chamber 96 of FIG. 2 at separate frequencies determined by the rpm of chopper disc 52.

Figure 5:
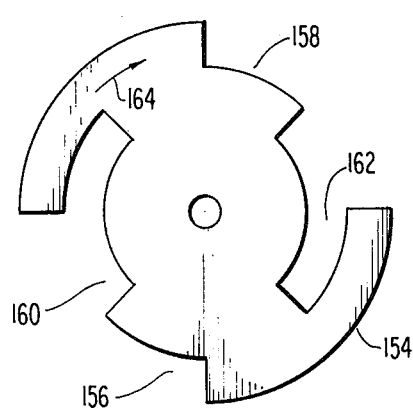

FIG. 5 shows a chopper disc 154 with the same number of outer and inner windows. These are two outer windows 156 and 158 each extending 90° circumferentially and located 180° out of phase with respect to each other and, two inner windows 160 and 162 each extending 90° circumferentially and located 180° out of phase with respect to each other. Inner windows 160 and 162 are out of phase with respect to outer windows 156 and 158 so the inner windows lead the outer windows by 45° when disc 154 is rotated clockwise in the direction of arrow 164. Selection of the chopper disc 52 of FIG. 4 or the chopper disc 154 of FIG. 5 is primarily related to the type of detector and its response time or lag.

Figure 6:
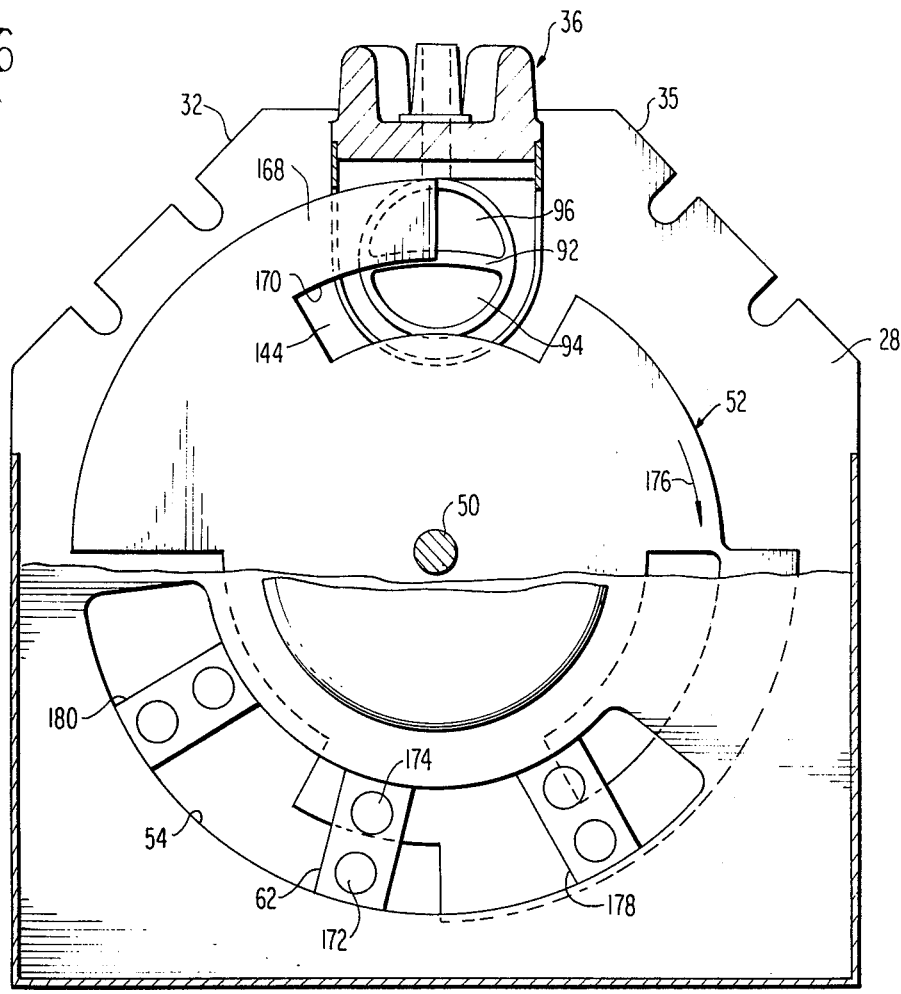

FIG. 6 shows the relationship between chopper disc 52, analyzer unit 36, and phototransistor mounting block 62. It will be seen from FIG. 6 that the height of reference gas chamber 94 as measured along a radius of disc 52 is approximately equal to the radial dimension of window 144 of the disc. Edge 170 of disc blade portion 168 is located at the center line of divider partition 92 which divides the cell structure into reference and sample chambers. The divider partition can curve circumferentially about the fixed center axis of rotation of disc 52, i.e. motor shaft 50. The various inner and outer windows have their inner and outer edges curving circumferentially with respect to the axis of shaft 50. This arrangement coupled with the curvature of divider partition 92 provides for free travel of radiation along either path when uncovered by a window of the disc and complete blocking of radiation along a path when covered by a solid portion of the chopper disc.

The multi-unit concept of the present invention utilizes the single chopper disc as part of the phase reference generating means. A phase reference signal generating detector is located in the travel path of the chopper windows for the sample gas path and the chopper windows for the reference gas path for each unit. Such detector responds to a single source of energy located on the opposite side of the chopper disc. The source of energy can be visible light so that light sensitive devices, such as phototransistors 172 and 174 are mounted in each phototransistor block 62. Slot 54 of partition 46 is so formed, relative to mounting block 62, that phototransistor 174 is mounted along the travel path of the inner windows 144-146 of disc 52 and phototransistor 172 is mounted along the travel path of outer windows 140 and 142 of the disc. Rotation of disc 52 chops not only the infrared radiation in the gas analyzer unit but also the light emanating from bulb 64. The light sensing detectors can be symmetrically opposite the gas paths of gas analyzer unit or as shown in FIG. 6. In that embodiment transistor block 62 is not symmetrically opposite the location of the sample and reference gas paths but is circumferentially spaced a distance greater than 180° in the direction of rotation of disc 52. Postioning depends on detector response time. For relatively fast detectors, such as lead selenide detectors, the 180° symmetrical position can be used; relatively slow thermopile detectors use the circumferentially spaced location to compensate for detector lag. Each phototransistor block can have flat support shoulders 61 permitting force fit in slot 54 of partition 46. Each block is made of electrical insulating resilient material. This enables shifting the blocks as required to obtain the desired synchronous signal generation. Other types of slot mounting means and phototransistor support blocks than those illustrated can be used to carry out the multi-unit gas analyses concept of the present invention.

Additional gas analyzer units such as unit 36 can be seated on edges 32 and 35 of rear wall 28 and can be spaced respectively at an angle of 45° to each side of the unit 36 shown at FIG. 6. With disc 52 rotating counterclockwise, phototransistor block 178 operates with the unit placed on edge 32 and phototransistor block 180 operates with the unit placed on edge 35. The phototransistor blocks are adjustably mounted along the circumferential path about the axis of rotation of the chopper disc to permit selective synchronous phase signal generation.

A single chopper disc acts as a chopper common to the plurality of gas analyzer units permitting multiple gas or multiple constituent analysis of the same gas simulataneously. The phototransistors 172 and 174 cooperate with chopper disc 52 and signal separation circuitry to separate the sample and reference path electrical signals from the single detector 122. In accordance with the invention meaningful information indicative of the quantity of a particular gas in sample chamber 96 can be precisely determined by comparison of such separated signals in various mathematical relationships.

During rotation of disc 52, infrared radiation passing through reference chamber 94 and sample chamber 96 is chopped. Chopping of the sample gas path can occur at a frequency different from chopping of the reference gas path dependent on selection of the chopper disc. The infrared radiation from both paths which falls on detector 122 causes the detector to generate an electrical output indicative of the total amount of radiation which reaches the detector.

The electrical output of detector 122 is separated by a unique phase sensitive separation arrangement which enables identifying that component of the infrared energy passing through sample chamber 96 with respect to the infrared energy which passes through reference chamber 94. Separate channels are provided for the reference and sample gas path signals. The combined output of the single detector is separated in these channels which are gated by the phase reference signals from phase detector elements such as the phototransistors described above. Other phase reference generating means could be used, e.g. magnetic pickup devices or devices utilizing other types of radiant energy.

Referring to FIG. 7, the signal which appears at output line 200 of detector 122 is an alternating signal as a result of the chopping action of chopper disc 52. This signal is amplified by a preamplifier 202 in series with a capacitor 204 so that only alternating current signals pass to junction 205.

To carry out the novel separation provided by the invention, the signal at juncture 205 is fed into phase demodulator circuit means including two separate electrical channels, one for the sample gas path and one for the reference gas path. Each of such channels includes circuit means for receiving dual electrical inputs. Such inputs include the combined sample and reference path output signal from the infrared detector and a signal through a gating device when it is conducting. Each channel effectively combines these inputs and produces an average voltage output responsive to its respective gas path signal. In this arrangement each channel includes an amplifier which is operative during passage of infrared in both the sample and reference gas paths thereby avoiding complete on and off operation which would occur if each amplifier were responsive only to its respective gas path passage of infrared. The respective output of each channel is a more accurate indication of infrared passage in its respective gas path due to increased stability of the electronics which helps reduce the effects of any non-linearity of the amplifier means.

To describe this operation in more detail: junction 205 is connected to an inverting amplifier 208 via resistor 210. The feedback resistor 212 has the same value as resistor 210 so amplifier 208 has the effect of merely inverting the signal appearing at junction 205, or differently stated, has the effect of multiplying the signal by −1. The signal then passes to a field effect transistor (FET) 214 via resistor 216. FET 214 functions as a gating device for passing the signal to input terminal 218 of operational amplifier 220 when FET 214 is conducting. The novel separation means make provision that the signal at junction 205 can reach input terminal 218 of operational amplifier 220 via the path including amplifier 208 and field effect transistor 214 when the field effect transistor is conducting; also the signal appearing at junction 205 can at all times reach input terminal 218 via the path including line 222 and resistor 224.

Amplifier 220 has a resistor 226 connected in series with output terminal 228 of amplifier 220 via potentiometer 230. The ratio of the value of resistor 224 to the combined feedback resistances of resistor 226 and the portion of potentiometer 230 between output terminal 228 is approximately 1:1. On the other hand, the ratio feedback resistance of the effective part of potentiometer 230 and resistor 226 to resistor 216 is approximately 2:1. The effect of this arrangement is that signals appearing at input terminal 218 of amplifier 220 via the path including resistor 224 are simply inverted (or multiplied by −1) whereas signals appearing at input terminal 218 via FET 214 are inverted and multiplied by a factor of 2 (are multiplied by −2).

The signal at output terminal 228 of amplifier 220 passes through, and is filtered i.e. averaged, by the filter means including resistors 232 and 234 and capacitor 235.

The components of FIG. 7 described immediately above form one electrical channel of the circuit means; such channel means are delineated by dotted lines and designated 236. The second channel includes the components within dotted lines designated 238. Components within channel means 238 have the same values as and are substantially identical to the corresponding components in channel means 236. Feedback resistor 240 has the same value as resistor 242 so signals appearing at input terminal 244 of amplifier 246 via resistor 242 are simply inverted or multiplied by −1. The ratio of resistor 240 to resistor 248 is 2:1 so signals through FET 250 are multiplied by a factor of 2 and are also inverted by amplifier 246, when FET 250 of channel means 238 is conducting.

Channel means 236 can be utilized as the reference or sample channel and channel means 238 can be utilized as the sample or reference channel. Potentiometer 230 can be located in either channel. Potentiometer 230 can be adjusted to balance the channels electrically. In addition, because of potentiometer 230 only resistors 210, 240, 242, and 248 need by 1% precision resistors.

For purposes of explanation channel 236 is designated as the sample gas path channel because its gating element 214 is activated by phototransistor 172 which is in the sample gas window path of the chopper. Sample channel 236 has its FET 214 gated "ON" in synchronism with the two outer windows of chopper 52 whereas reference channel 238 has its FET 250 gated "ON" in predetermined synchronism with the three inner windows of chopper disc 52. Phase sensitive separation can be facilitated by use of separate frequencies for the sample and reference paths by utilization of the proper chopper disc while utilizing the basic phase sensitive separation described.

The separate sample and reference channels are gated by the phototransistor means through bistable circuit means. The conduction of FET 214 is controlled by phototransistor 172 and conduction of FET 250 is controlled by phototransistor 174. Phototransistor 172 is connected in a symmetrical circuit arrangement 252 with NAND gate latch 256 which provides a square wave output. The symmetrical circuit 252 is so arranged that when transistor 172 conducts there is a decrease in voltage (to a logic 0 level) at junction 258 and there is an increase in voltage (to a logic 1) level at junction 260. When phototransistor 172 becomes nonconducting the voltage at junction 260 decreases (to logic 0) and the voltage at junction 258 increases (to a logic 1 level). Correspondingly, whenever phototransistor 172 is illuminated so it becomes conducting, the output signal at terminal 262 of NAND gate 256 is at a high level (logic 1) and the output at terminal 264 is at a low level (logic 0). Since the two NAND gates are tied back to back, the output at terminal 262 will remain high to maintain FET 214 conducting until there is a transition of voltage from a high level to a low level at junction 260 (becomes logic 0). This transition at junction 260 occurs when phototransistor 172 receives no light from bulb 64. Simultaneously, the voltage level at junction 258 increases from a low to a high level. Correspondingly, when phototransistor 172 is dark, terminal 262 has a low output (logic 0) and terminal 264 has a high output (logic 1). With phototransistor 172 dark, FET 214 is nonconducting.

If it is desired to have FET 214 gated on when phototransistor 172 is dark, it would merely be necessary to connect gate line 265 to terminal 264 of the NAND gate latch 256.

The circuitry and NAND gate latch arrangement for phototransistor 174 and its associated latch circuit 266 are identical in operation to that described for phototransistor 172, and output terminal 268 of latch 266 corresponds to output terminal 262 of latch 256. Correspondingly, when phototransistor 174 is illuminated the voltage of terminal 268 is high, or logic 1, and FET 250 conducts.

When the diametrically opposite outer windows 140 and 142 of chopper disc 52 permit infrared radiation to pass through sample chamber 96, FET 214 is gated "ON"; when the disc 52 blocks the path of IR through sample chamber 96, FET 214 is nonconducting. Because of the negative symmetry of inner windows 144-146 of disc 52, phototransistor 174 is dark when the windows 144-146 allow IR to pass through reference chamber 94. Hence, FET 250 is nonconducting whenever IR passes through the reference chamber and is conducting whenever IR is block from the reference chamber by disc 52.

The amplified detector signal appearing at junction 205 is the composite of the total detector response resulting from radiation in both the sample chamber 96 and the reference chamber 94. This can be designated $V_s + V_r$; $V_s$ being the detector response resulting from IR passing along the sample gas path and $V_r$ being the detector response from IR passing along the reference gas path. By virtue of the −1 multiplication function of amplifier 220 for signals appearing at input terminal 218 via line 222 and resistor 224, the signal at output terminal 228 is $-(V_s + V_r)$ whenever FET 214 is nonconducting. By virtue of the inverting function of amplifier 208, the signal appearing at its output terminal 211 is $-(V_s + V_r)$. When FET 214 is conducting, and because of the −2 multiplication of amplifier 220 of signals appearing at junction 218 via the path including FET 214 and resistor 216, amplifier 220 functions also as an adder to add the quantity $(V_s + V_r)$ from resistor 224 to the quantity $-(V_s + V_r)$ while multiplying the quantity $-(V_s + V_r)$ by −2 so that the signal at output terminal 228 is $+2(V_s + V_r) - (V_s + V_r)$ which equals $V_s + V_r$ when FET 214 is conducting.

The following description of FIGS. 7A through 7J brings out that the signal appearing at output terminal 228 is the average voltage $V_s$, indicative of radiant energy passage in the sample gas path and that the signal appearing at output terminal 247 of amplifier 246 is the average voltage $-V_r$, indicative of radiant energy passage in the reference gas path.

Figure 7A:
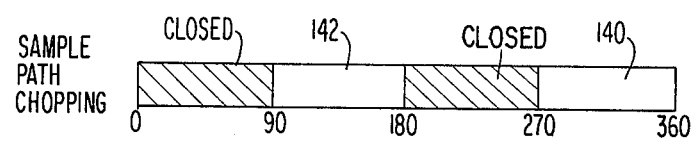

FIG. 7A shows the result of chopping in the sample gas path during one revolution of disc 52. It will be seen that clockwise rotation of the disc from the position shown at FIGS. 4 and 6 results in windows 142 and 140 passing IR through the sample cell for a total of 180° of rotation. These windows pass IR through the sample gas cell between 90° and 180°, and between 270°-360°.

Figure 7B:
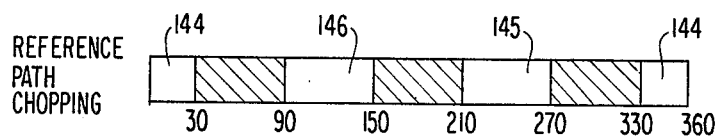

FIG. 7B shows the result of chopping in the reference gas path during one revolution of disc 52.

Figure 7C:
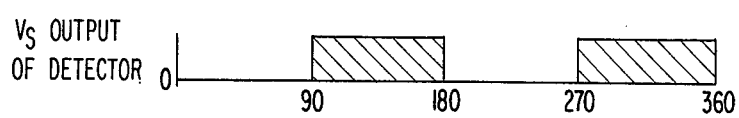

FIG. 7C shows the response of the detector as a result of IR passing through windows 142 and 140 in the sample gas path.

Figure 7D:

FIG. 7D shows the response of the detector as a result of passage of IR through windows 144-146 in the reference gas path.

Figure 7E:
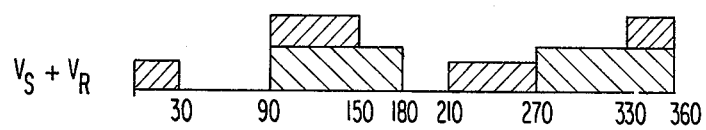

In FIG. 7E the detector response of FIG. 7C and of FIG. 7D are added together to show the total output of the detector.

Figure 7F:
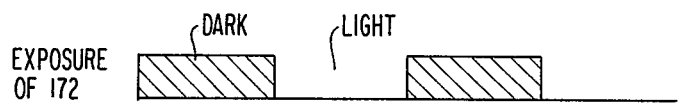

FIG. 7F shows the "ON" intervals of the sample gas path of transistor 172, which are in phase with response of FIG. 7C.

Figure 7G:

FIG. 7G shows the "ON" intervals of reference gas path phototransistor 174 which are out of phase with respect to the reference path detector response.

As previously explained, when FET 214 is nonconducting, the signal at the output of terminal 228 is $-(V_s + V_r)$, and when FET 214 is conducting the signal at output terminal 228 is $(V_s + V_r)$.

Figure 7H:
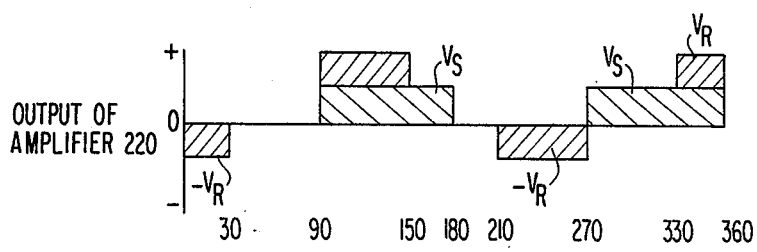

FIG. 7H shows the signal at output terminal 228 for one complete revolution of disc 52. During the first 90° of rotation of disc 52 from its position of FIG. 6, FET 214 is nonconducting, and as a result simply inverts the $V_s + V_r$ occurring during the first 90° of detector output, which, as shown at FIG. 7E, is 30° of $V_r$. During the second 90°, i.e. 90°-180° rotation of the disc, FET 214 is "ON" and passes the output of the detector shown at FIG. 7E between 90° and 180° during that interval. From 180°-270°, FET 214 is "OFF" so the detector output of FIG. 7E is inverted during that interval to provide the $-V_r$ between 210° and 270° as shown at FIG. 7H. From 270°-360° FET 214 is again conducting so the entire detector output signal is realized at the output of amplifier 220. It will be seen from FIG. 7H that the positive reference path outputs cancel the negative reference path outputs and the result at terminal 228 is the $V_s$ signal for 180° of rotation of disc 52.

Figure 7J:
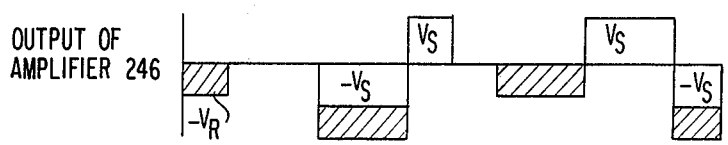

Similarly, as shown at FIG. 7J the sample path signals all cancel out as a result of the inversions of the amplifiers 208 and 246, and the gating of FET 250, the resulting output being $-V_r$ for 180°. The outputs of FIGS. 7H and 7J representing $V_s$ and $-V_r$ are the outputs obtained as a result of averaging the respective signals at output terminals 228 and 247 for one complete revolution of the chopper disc. Such averaging is accomplished with the filters at the respective outputs 228 and 247 of the amplifiers 220 and 246. The resultant, at summing junction 274, is $V_s - v_r$. When the $V_s - V_r$ signal is amplified and inverted by amplifier 276, the resulting output function if $V_r - V_s$. $V_r$ provides a "dynamic zero" $(V_r - V_s = 0)$ when there is no absorbing gas of interest in the sample chamber. Correspondingly, absorption of IR in the sample chamber changes $V_s$, while $V_r$ remains constant, and the resulting voltage output is an accurate representation of the sample chamber absorption. This can be indicated directly in terms of % gas of interest on a suitably calibrated indicator, such as a D'Arsonval meter, or an appropriate recording instrument.

In order to obtain the desired output function, $(V_r - V_s)$ with the disc 154 of FIG. 5 where both the inner and outer windows are 180° out of phase so both phototransistor 172 and phototransistor 174 are in phase with the light passing through the respective sample and reference cells, the gate of FET 250 is connected to output terminal 261 of NAND latch 266 to reverse the phase of the phototransistor output with respect to the windows 156 and 158. Such a connection is shown in dotted lines on FIG 7. It can be shown that the voltage appearing at output terminal 228 of amplifier 220 is $V_s$ and that the voltage at output terminal 247 of amplifier 246 is $-V_r$. The output of inverting amplifier 276 is the algebraic difference between the desired $V_s$ and $V_r$. Resistor 278 establishes the D.C. gain amplifier 276 and capacitor 280 provides additional integration or averaging of the resulting output signal.

To assure that the circuitry of FIG. 7 is operative and is not merely emitting a zero output voltage because it is inoperative or inactive, solenoid 128 can be actuated by the operator of the equipment to block a predetermined portion of the path of infrared radiation through the sample chamber. Then if the meter does not move appropriately to a predetermined calibration position, the operator knows that the equipment is defective. The calibration position, with solenoid 128 energized, can be used to adjust potentiometer 230 to balance the system output. Alternatively, adjustable voltage dividers can be used for this purpose.

The gas analyzer 300 of FIG. 8 is particularly adapted for analyzing ambient air or gas which is made to flow through the apparatus as indicated by arrow 302. Apparatus 300 includes IR source 304 which directs its radiant energy to a mirror 306 from which it is directed to a second mirror 308. The latter focuses the IR on detector 310. A window 312 seals the enclosure 314 in which detector 310 is located and a window 316 seals the enclosure for IR source 304. Windows 312 and 316 define precisely equal absorption sample gas and reference gas path lengths for gas flow between the source and detector so that accurate analysis of the gas passing between the windows can be made.

In accordance with the invention filters define the sample and reference gas paths. These filters are mounted in chamber 314 and include a semicircular sample beam filter 318 and semicircular reference beam filter 320 in opposed relation to filter 318. The beam path designated by arrows 322 is the sample beam path and the beam path designated by arrows 324 is the reference beam path.

In order to make this unique arrangement workable, the sample beam filter 318 is chosen to transmit in the absorption band of the gas being measured. For example, where carbon dioxide is being measured, filter 318 is chosen to transmit in a band of from 4.2–4.3 microns ($\mu$m). Reference beam filter 320 is selected to transmit in a nearby non-absorbed wave length band, e.g. in the range of 4.4–4.5 $\mu$m in which the total gas mixture under analysis is transparent. Since the infrared originating in each path is the same strength, and because of filter 318, only the sample gas path is affected by the gas of interest (carbon dioxide), the transmission of IR in the sample path is a direct measurement indication of the carbon dioxide percentage of ppm above zero.

Both sample beam 322 and reference beam 324 are chopped, e.g. by chopper disc 52. Phototransistors 326 and 328 are positioned on the opposite side of chopper disc 52 from a light source 330. Rotating chopping disc 52 at approximately 300 rpm so the sample beam is chopped at the rate of 10 hertz and the reference beam is chopped at the rate of 15 hertz provides an output from detector 310 which can be fed to the circuit of FIG. 7 to obtain the desired algebraic difference between $V_s$ and $V_r$ which is fed to the calibrated meter or recorder.

The FIG. 8 gas analyzer can be arranged to be supported by a multi-unit gas analyzer so that several gas constituents can be analyzed simultaneously. One or more of the remaining gas analyzers can include the closed chamber gas paths described earlier.

Both chamber 314 containing detector 310 and chamber 315 containing IR source 304 are filled with a non-absorbing gas, such as nitrogen or argon, and hermetically sealed. An adjustable trim tab 332 can also be provided in the sample path 322 to provide compensation for slight differences in the optical paths and characteristics of the filters 318 and 320.

Gas analyzer unit 350 of FIG. 9 is also used for analyzing an ambient atmosphere. Unit 350 is somewhat similar to the arrangement of FIG. 8 and the same designating numerals are used for corresponding elements such as IR source 304, columnating mirrors 306 and 308, IR detector 310 and reference and sample path beams 322 and 324. However, reference beam 324 passes through a reference cell 352 while the sample path 322 is open and unobstructed. A gas analyzer equipped with cell unit 350 can simply be placed at a desired location such that IR from source 304 passes through the ambient atmosphere. The portions of the sample and reference gas paths which are longitudinally beyond the reference gas chamber 352 balance each other out. Phototransistor 326 and 328 receive light from lamp 330, and the output of detector 310 is connected to the circuit of FIG. 7 to obtain the desired algebraic difference between $V_s$ and $V_r$. A calibrating tab 356 can be provided in sample path 322 to initially calibrate cell unit 350. The cell unit can be used with a multiple unit housing.

Optical gas analyzer system 360 of FIG. 10 includes an IR source 362 which can be the same as source 304 of FIGS. 8 and 9. There is also an IR detector 364 which can be the same as detector 310. The infrared radiation from source 362 is columnated by a lens 366 into sample and reference beams 368 and 370 which pass respectively through a sample chamber 372 and a reference chamber 374. Chambers 372 and 374 can be identical to the sample and reference chambers 96 and 94 of FIGS. 1–4. Sample chamber 372 includes suitable ports 376 for passing the gas of interest through the sample chamber. The gas in reference chamber 374 can have characteristics of and a percentage approximately midway in the range of the percentage to be determined for the gas of interest. Infrared radiation passing through the reference and sample chambers if focused by a focusing lens 378 onto detector 364 and passes through an optical filter 380. Optical filter 380 is selected so it transmits only IR radiation in the absorption band of the gas of interest; for example for carbon monoxide a filter centered at 4.7 microns; for hydrocarbon a filter centered at 3.4 microns. Chopper disc 52 rotates to chop both beams 368 and 378 in the manner previously described. Suitable phototransistors 326 and 328 are mounted on the opposite side of disc 52 from light source 330 to provide the phase separation signal for the circuitry of FIG. 7.

The circuitry of FIG. 7 described thus far can be used to provide an algebraic difference between $V_s$ and $V_r$. Also, the basic circuit of FIG. 7 can be used to introduce an automatic gain control function. FIGS. 11–13 introduce the AGC function by electronic ratio means. FIG. 14 introduces the AGC function with feedback means.

FIG. 11 shows a modification of a portion of the circuit of FIG. 7 which obtains the ratio $V_s/V_r$ in order to eliminate the effect of variations in source intensity, preamplifier gain, attenuation in the optical path, and other components which affect both the sample and reference gas paths equally. Line 384 is connected to output terminal 228 of amplifier 220 of the arrangement of FIG. 7 and line 386 is connected to output terminal 247 of amplifier 246. The signals $V_s$ appears on line 384 and the signal $-V_r$ appears on the line 386. The respective signals pass through filters 388 and 390 and then to divider 392 which divides $V_s$ by $-V_r$ so the output of the divider is $-V_s/V_r$. The arrangement of FIG. 11 can include an amplifier 395, gain determining resistor 396, and capacitor 397 to integrate or further average the signal which passes to meter 394. Amplifier 395 inverts the $-V_s/V_r$ signal so the output to meter 394 is $V_s/V_r$.

FIG. 12 shows a modification of the circuit of FIG. 7 which can be used to obtain the ratio $V_s-V_r/V_r$. The circuit of FIG. 12 is connected to output terminals 228 and 247 of the respective amplifiers 220 and 246 of the circuitry of FIG. 7. Sample path signal $V_s$ is filtered by filter network 388 and reference path signal $-V_r$ is filtered by filter network 390. The respective signals $V_s$ and $-V_r$ are fed to a summing amplifier 402 whose output becomes $V_s - V_r$. The signal $-V_r$ passes along line 404 to divider 406 which also receives the output signal $V_s - V_r$ from summing amplifier 402. The output line 408 of divider 406 receives the signal $-(V_s -V_r)/V_r$ which passes through amplifier-integrator arrangement 410 that inverts the signal to $V_s -V_r/V_r$ and is connected to meter 412, calibrated directly in the percentage of the gas of interest.

FIG. 13 shows electronics for obtaining the ratio $V_s -V_r$ over $V_s + V_r$. In the embodiment of FIG. 13 the $V_s$ signal at output terminal 228 is filtered by filter network 388 and the reference signal $-V_r$ is filtered by filter network 390. The $V_s$ and $-V_r$ signals pass to a summing amplifier 414, the output of which is $V_s - V_r$. The $-V_r$ and $V_s$ signals are also fed to a difference amplifier 416 the output of which is $V_s + V_r$. The $V_s - V_r$ signal from summing amplifier 414 is divided by the $V_s + V_r$ output of difference amplifier 416 to obtain the desired ratio $(V_s - V_r)/V_s + V_r)$ at the output of divider 418. The resulting signal is amplified and integrated by amplifier arrangement 420 and fed to indicating meter 422.

FIG. 14 shows a novel feedback arrangement for providing automatic gain control. A feedback network 450 (shown in dotted lines) is connected to the reference gas path output terminal 247 of amplifier 246 of FIG. 7. The output at terminal 247 through the feedback network 450 is connected to the separating electronics so as to be introduced into both the sample gas and reference gas path electrical channels 236 and 238 of FIG. 7.

The feedback network 450 includes an integrating amplifier 452 having one of its inputs connected to output terminal 247 and having its other input connected to a potentiometer 454 which functions as a scale factor potentiometer. Integrating amplifier 452 compares the average level of the signal $-V_r$ with the voltage on line 456 from potentiometer 454. Any deviation in the averaged $-V_r$ signal from terminal 247 causes amplifier 452 to generate an error signal which is fed back to the input of the separating electronics through variable gain amplifier 458.

The effect of the feedback signal to input 460 of the variable gain amplifier is to vary the gain of the amplifier in such a manner as to maintain the reference voltage $-V_r$ at terminal 247 essentially constant and equal to the voltage from potentiometer 454. The ultimate effect is to reduce the affect of variations in characteristics such as the source temperature, optical transmission, detector responsivity, and amplifier gain. Maintaining the $-V_r$ signal at output terminal 247 essentially constant eliminates the effect of such variables which affect both paths of the system equally. Better signal to noise ratio and better stability is obtained with the circuit of FIG. 14 as a result of the feedback arrangement.

Typical applications for the invention include measurement of internal combustion exhaust emission for carbon monoxide and hydrocarbons; testing of controlled atmospheres, such as furnaces or growth chambers for carbon dioxide, carbon monoxide, hydrocarbons, ammonia, and water vapor for combustion control or process stream analysis; monitoring of air quality, biological analysis such as making the analyzer the sensing element of a continuous flow respirometer measuring carbon dioxide, and measurement of methane in oil and gas well drilling.

A sensitive, low noise circuit is provided with fast response, high gain stability, and low drift. For example, with the present invention accurate gas analysis readings can usually be obtained in about 5 seconds; electronic noise level is less than 1% of full scale, and accuracy of plus or minus 1% of full scale is provided when the circuit is used with a recorder. The accuracy of the instrument is maintained over the ordinary range of ambient temperature. Sensitivity characteristics of the present invention are represented by the discrimination available; for example, when measuring carbon monoxide, the response to 20% carbon monoxide, or 2000 ppm hexane, or 80% relative humidity (at 70°F.) is less than 0.1% in the carbon monoxide reading; when measuring hydrocarbons, the response to 10% carbon monoxide, or 20% carbon dioxide, or 80% relative humidity (at 70°F.) is less than the equivalent 10 ppm hexane in the hexane reading.

The basic multi-unit concept involves use of a plurality of single source and detector gas analysis assemblies mounted to be operative with a single chopper disc which also coacts with phase reference signal generating means by chopping the type of energy used in that phasing system is predetermined synchronous relationship with chopping of the radiation absorbed in the optical gas paths. The basic circuit directs the total response of the single detector for each unit, as an AC signal, to demodulator circuit means. Separate electrical channels for the sample and reference gas paths utilize the combined AC signal and switching driver means including a gating element connected through bistable circuit means to the phase reference generating means to separate the combined signal and provide average voltage values, $V_s$ and $V_r$, for the sample and reference gas paths. Use of the combined detector output in both channels and an automatic gain control function contribute to the stability and accuracy of the circuit.

Other bistable circuit means than the specific circuit shown in FIG. 7 can be used to connect the phase reference generating means to the gating element, such bistable switching means should provide a square wave output for fast switching.

With the information in the present disclosure changes in structural details or substitution of other circuit element equivalents can be made by those skilled in the art without departing from the scope of the invention. Also, while infrared source, detector, and filter means have been specifically described, it should be clear that gases responsive to other radiant energy, such as visible light or ultraviolet, can be adapted to the above disclosure with appropriate changes in radiation source, detector, and filters. Therefore the scope of the present invention is not to be limited to the specific embodiment described but is to be determined from the appended claims.

What is claimed is:
1. Gas analyzing structure for use in simultaneously performing multiple gas anaylses comprising
  frame means supporting a plurality of individual optical gas anaylsis assemblies located to dispose portions of each such assembly along an arcuate path, each such assembly of said plurality of assemblies including a single source of radiant energy, a single radiant energy detector having an electrical output, means for directing the radiant energy from the single source for passage along a sample gas and a reference gas path, and means for directing such radiant energy after passage along the reference gas and sample gas paths to the single detector for such radiant energy, means for predetermined cyclic interruption of radiant energy in the sample and reference gas paths of each such assembly including a single chopper disc rotatable about a fixed central axis located in predetermined positional relationship to the arcuate path disposition of gas analysis assemblies, the chopper disc including a plurality of windows predeterminedly spaced radially from the fixed central axis with a portion of the windows being spaced from the central axis a predetermined distance to permit passage of radiant energy in the sample gas path and a portion of the windows being spaced radially from the central axis to permit passage of radiant energy in the reference gas path of each optical gas analyzer assembly upon rotation of the chopper disc about the fixed central axis, and said radiant energy detector of each of said assemblies being adapted to be connected to circuitry for processing the electrical output of a detector.

2. The structure of claim 1 in which the predetermined arcuate path of disposition of the portion of each optical gas analysis assembly is along a substantially circumferential path about the fixed central axis, and further including drive means for rotating the chopper disc.

3. The structure of claim 1 including in combination phase reference signal generating means on said frame means and responsive to rotation of the single chopper disc for generating electrical phase reference output in predetermined synchronous relationship with cyclic interruption of radiant energy in the sample and reference gas paths.

4. The combination of claim 3 further including circuit means connected to the detector of each optical gas analysis assembly for providing phase-sensitive separation of the electrical output from the single detector in each such optical assembly into electrical signals indicative of radiant energy passage in the sample and reference gas paths, and means connecting the output of the phase reference signal generating means to the circuit means providing the phase-sensitive separation of the electrical output of the detector in such gas analysis assembly.

5. The device of claim 1 in which the sample and reference gas paths are defined by cell structure with divider means separating the cell structure into a sample gas chamber and a reference gas chamber, such chambers being in contiguous aligned relationship extending longitudinally between the single source of radiant energy and the single detector for such radiant energy.

6. The structure of claim 1 in which the single source of radiant energy comprises an infrared source and the single detector comprises an infrared detector.

7. The structure of claim 6 including
filter means for selective passage of infrared radiation in both the reference and sample gas paths of at least one of the gas analysis assemblies, said filter means having common infrared transmitting characteristics.

8. The device of claim 6 in which at least one of the optical gas analysis assemblies includes
selective frequency filters for infrared energy, such selective frequency filters defining the sample and reference gas paths such that ambient gas being analyzed flows in the space between the single infrared source and the single infrared detector of such assembly.

9. The device of claim 1 in which at least one of the optical gas analysis systems includes a reference gas chamber extending longitudinally between the source and detector so as to define the reference gas path, and the sample gas path is open for analysis of ambient atmosphere between the source and detector.

10. Gas analyzing apparatus providing sample and reference gas path comparison data comprising
single source means for radiant energy to be absorbed by the gas under analysis,
means for directing such radiant energy from the single source means along a sample gas path and a reference gas path,
chopper disc means located in the sample and reference gas paths providing predetermined cyclic interruption of radiant energy in each such path,
synchronizing means cyclically actuated by the chopper disc means to generate electrical output in predetermined phase relationship with passage of radiant energy in the sample gas path and in the reference gas path,
single detector means positioned to receive radiant energy from each such path after cyclic interruption and to generate electrical output responsive to the radiant energy passage along both the sample and reference gas paths,
circuit means electrically connected to the single detector means,
such circuit means including a separate electrical channel means for the sample gas path and for the reference gas path,
each such separate electrical channel means including amplifier means,
each such amplifier means having input juncture means and output juncture means,
the circuit means electrically connected to the single detector means further including phase-sensitive circuit means for each electrical channel means,
each such phase-sensitive circuit means including an electrical gating device actuated by the electrical output of the synchronizing means of its respective gas path in predetermined phase relationship to actuation of the gating device in the remaining gas path to gate signals from the detector means to the amplifier means along a predetermined path,
each said gating device being connected to the input juncture means of its respective electrical channel amplifier means to define one electrical path from the detector means to such amplifier means,
each such electrical channel means including an additional electrical path from the detector means to the input juncture means of its respective amplifier means such that each channel amplifier means operates responsively to sample and reference gas path signals with the result that
the sample gas path electrical channel means combines sample path gating device signals and the additional electrical path signals at the channel amplifier means to effectively eliminate reference gas path detector output signals to produce a signal, $V_s$, indicative of the signal generated by the detector as a result of radiant energy passage along the sample gas path, and the reference gas path channel combines reference gas path gating device signals and the additional electrical path signals at its channel amplifier means to effectively eliminate sample gas path detector output signals to produce a signal, $V_r$, indicative of the signal generated by the detector as a result of radiant energy passing along the reference path, said $V_s$ and $V_r$ signal appearing at the output juncture means of the respective amplifier means, means connected to the output juncture means of the amplifier means for averaging respective $V_s$ and $V_r$ signals, and output circuit means for producing an output representative of a comparison of the passage of radiant energy through the reference gas and the sample gas paths.

11. The gas analyzing apparatus of claim 10 in which the output circuit means includes means for determining the algebraic difference between $V_s$ and $V_r$.

12. The gas analyzing apparatus of claim 10 in which the output circuit means includes electronic ratio means providing an automatic gain control function to compensate for variations in the intensity of the radiant energy source, attenuation in the optical path, and component variations.

13. The gas analyzing apparatus of claim 12 in which the electronic ratio means provides a ratio based on the values of $V_s$ and $V_r$.

14. The gas analyzing apparatus of claim 12 in which the electronic ratio means provides a ratio based on the values $(V_s - V_r)$ and $V_r$.

15. The gas analyzing apparatus of claim 12 in which the electronic ratio means provides a ratio based on the values $(V_s - V_r)$ and $(V_s + V_r)$.

16. The gas analyzing apparatus of claim 10 further including feedback means connected to an output of the electrical channel means for the reference gas path, and means connecting the feedback means to the circuit means electrically connected to the single detector means to provide automatic gain control to compensate for variation source intensity, attenuation in the optical path, and component variations which influence both gas paths equally.

17. The gas analyzing apparatus of claim 10 in which the synchronizing means includes a light-sensitive device for producing synchronizing signals in synchronism with the cyclic interruption of radiant energy for each gas path, bistable latch means for each ligh-sensitive device for shaping output signals of such devices, symmetrical circuit means connecting the light-sensitive device of each gas path to its bistable latch means, the bistable latch means each having dual outputs in negative symmetry, and means for connecting one output of each bistable latch means to the gating device of its corresponding electrical channel means.

18. The gas analyzing apparatus of claim 10 in which the synchronizing means includes first and second light sensitive devices, shaping circuit means connected to each light-sensitive device for shaping output signals of such devices, circuit means for switching such shaping circuit means in response to a change in illumination of its light-sensitive device, window means in the chopper disc for chopping the sample gas path, and window means in the chopper disc for chopping the reference gas path, means mounting one of the light-sensitive devices adjacent to the travel path of the window means for the sample gas path, means mounting the other light sensitive device adjacent the travel path of the window means for the reference gas path, said light sensitive devices being in spaced relation to the sample and reference gas paths, such shaping circuit means connected to one light-sensitive device gating the gating device of one electrical channel means "ON" in response to illumination received by its light-sensitive device, and such shaping circuit means connected to the other light sensitive device gating the gating device of the other electrical channel "OFF" in response to illumination received by its light-sensitive device.

* * * * *